(12) United States Patent
Van Boeckel et al.

(10) Patent No.: US 6,875,755 B2
(45) Date of Patent: Apr. 5, 2005

(54) ANTITHROMBOTIC COMPOUND

(75) Inventors: Constant Adriaan Anton Van Boeckel, Oss (NL); Cornelis Maria Tromp, Ravenstein (NL); Tamara Theodora Maria Geertsen, Westervoort (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/148,868

(22) PCT Filed: Dec. 1, 2000

(86) PCT No.: PCT/EP00/12155

§ 371 (c)(1),
(2), (4) Date: Aug. 29, 2002

(87) PCT Pub. No.: WO01/42262

PCT Pub. Date: Jun. 14, 2001

(65) Prior Publication Data

US 2003/0114361 A1 Jun. 19, 2003

(30) Foreign Application Priority Data

Dec. 7, 1999 (DE) .......................................... 992 04 172

(51) Int. Cl.⁷ .......................... A61K 31/70; C07H 13/00
(52) U.S. Cl. .......................... 514/54; 514/25; 536/17.4; 536/17.5; 536/17.6; 536/123.1
(58) Field of Search ................................ 536/17.4, 17.5, 536/17.6, 123.1, 17.9, 124; 514/25, 54

(56) References Cited

FOREIGN PATENT DOCUMENTS

| WO | 99 25720 A | 5/1999 |
|---|---|---|
| WO | 99 65934 A | 12/1999 |

OTHER PUBLICATIONS

Buijsman, Rogier C. et al: "Design and synthesis of a novel synthetic NAPAP–pentasaccharide conjugate displaying a dual antithrombotic action" Bioorg. Med. Chem. Lett. (1999), 9(14), 2013–2018.

*Primary Examiner*—Elli Peselev
(74) *Attorney, Agent, or Firm*—Mark W. Milstead

(57) ABSTRACT

The present invention relates to compounds of the formula (I), wherein R is independently $SO_3^-$ or $CH_3$; the spacer is a flexible spacer of a length of 13–25 atoms; the charge of the pentasaccharide residue is compensated by positively charged counterions; and the total number of sulfate groups in the pentasaccharide residue is 4, 5 or 6; or a pharmaceutically acceptable salt, a prodrug or a solvate thereof. The compounds of the invention have antithrombotic activity and can be used in treating or preventing thrombin-related diseases.

8 Claims, No Drawings

ANTITHROMBOTIC COMPOUND

FIELD OF THE INVENTION

The invention relates to a new antithrombotic compound, a pharmaceutical composition containing the compound as an active ingredient, as well as the use of said compound for the manufacture of medicaments.

Formula (I):

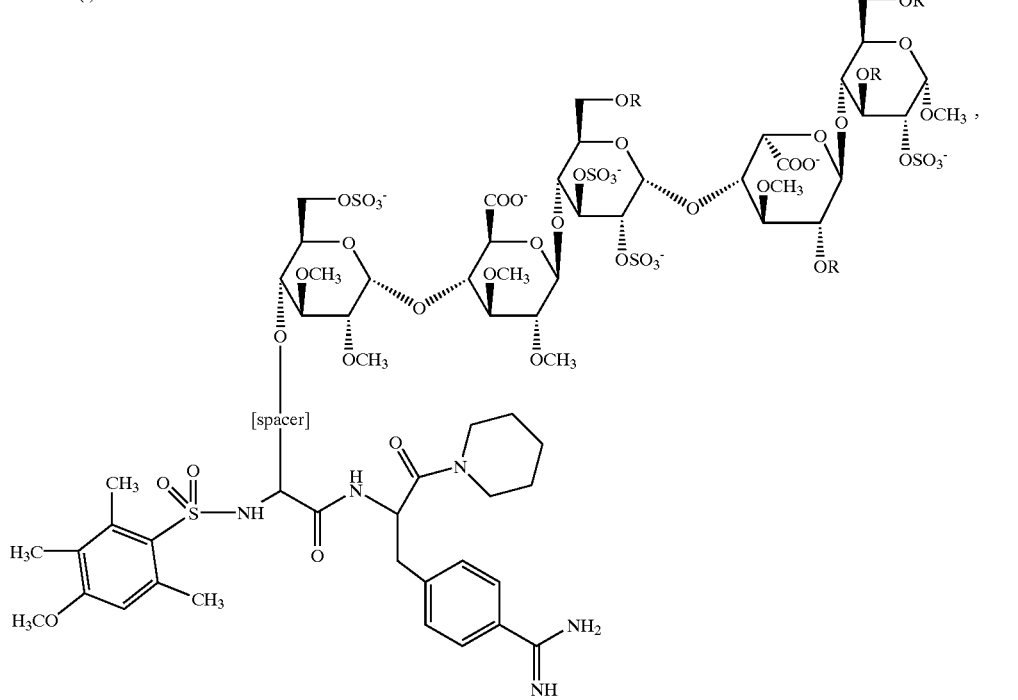

BACKGROUND OF THE INVENTION

Serine proteases are enzymes which play an important role in the blood coagulation cascade. An important serine protease is factor Xa, which catalyzes the conversion of prothrombin into thrombin. Thrombin is the final serine protease enzyme in the coagulation cascade. The prime function of thrombin is the cleavage of fibrinogen to generate fibrin monomers, which are cross-linked to form an insoluble gel. In addition, thrombin regulates its own production by activation of factors V and VIII earlier in the cascade. It also has important actions at cellular level, where it acts on specific receptors to cause platelet aggregation, endothelial cell activation and fibroblast proliferation. Thus thrombin has a central regulatory role in haemostasis and thrombus formation.

In the development of synthetic inhibitors of serine proteases, recently a synthetic NAPAP-pentasaccharide conjugate has been reported as antithrombotic having a dual profile of both direct anti-thrombin activity and ATIII-mediated anti-Xa activity (ATIII: antithrombin III) (Bioorg. Med. Chem. Lett. 1999, 9(14), 2013–8). Although the reported antithrombotic may be an interesting compound, HIT cross reactivity and neutralization by PF4 will be associated with this compound due to the high sulfate content of the pentasaccharide residue (Thromb. Haem. Suppl. 1997, p363 PD1485).

BRIEF SUMMARY OF THE INVENTION

It has now been found that the compounds of formula (I) are antithrombotics having an excellent and advantageous dual profile. The compounds of formula (I) have a pharmacological interesting half-life, allowing once-a-day treatment, and are hardly neutralized by PF4. Furthermore, bleeding risks are low. Altogether, the compounds of formula (I) have an attractive combination of pharmacological properties.

wherein R is independently $SO_3^-$ or $CH_3$;

the spacer is a flexible spacer of a length of 13–25 atoms, preferably 16–22, and most preferred 19 atoms;

the charge of the pentasaccharide residue is compensated by positively charged counterions;

and the total number of sulfate groups in the pentasaccharide residue is 4, 5 or 6;

or a pharmaceutically acceptable salt a prodrug or a solvate thereof.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The compounds of the invention may also be used as anticoagulants in extracorporeal blood circuits, as necessary in dialysis and surgery. The compounds of the invention may also be used as in vitro anticoagulants.

The compounds of formula (I) are specifically useful as antithrombotics for arterial indications.

DETAILED DESCRIPTION OF THE INVENTION

Preferred compounds according to the invention are compounds wherein the pentasaccharide residue has the structure:

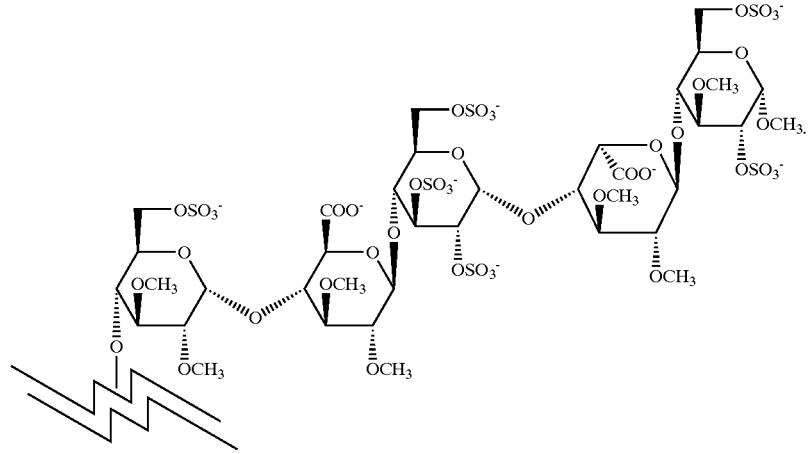

The chemical nature of the spacer is of minor importance for the anti-thrombotic activity of the compounds of the invention. However, the spacer of the compounds of the invention is flexible, which means that the spacer does not contain rigid elements, such as unsaturated bonds or cyclic structures. Suitable spacers may easily be designed by a person skilled in the art. Preferred spacers contain at least one —(CH$_2$CH$_2$O)— element. More preferred spacers contain three —(CH$_2$CH$_2$O)— elements. The most preferred spacer is *—(CH$_2$CH$_2$O)$_3$—(CH$_2$)$_2$—NH—C(O)—(CH$_2$)$_3$—NH—C(O)—CH$_2$—, the end indicated with * being attached to the pentasaccharide residue.

Preferred compounds of formula I are the compounds of (Ia), wherein p is 1–5, n is 1–5 and m is 1 or 2. The most preferred compound is the compound of formula (Ia), wherein p is 3, n is 3 and m is 1.

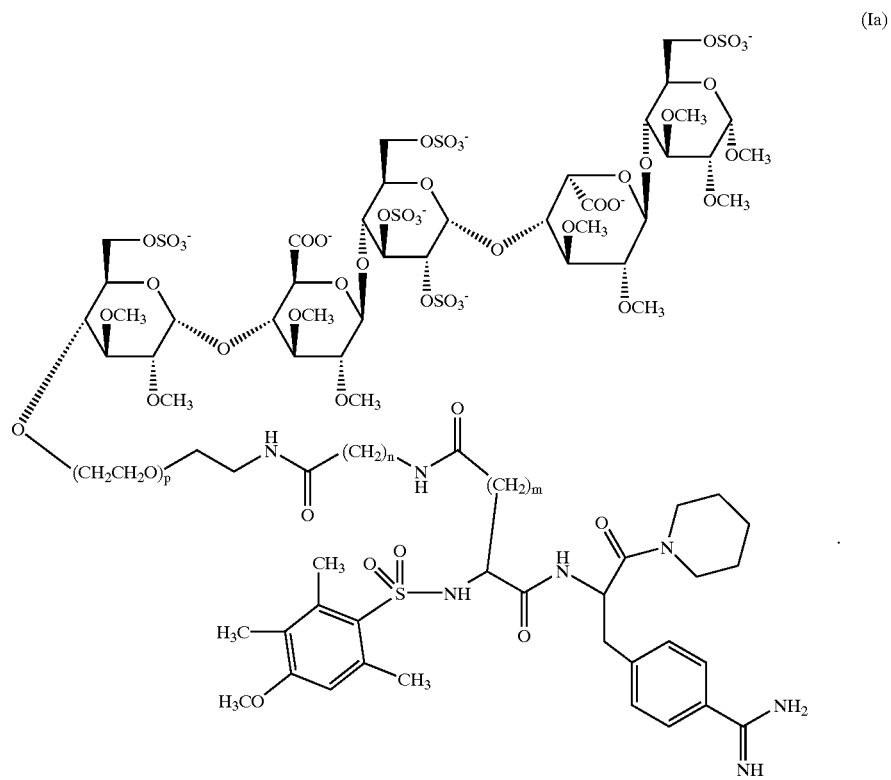

(Ia)

A positively charged counterion means H$^+$, Na$^+$, K$^+$, Ca$^{2+}$, and the like. Preferably the compounds of formula (I) are in the form of their sodium salt.

The term "prodrug" means a compound of the invention in which the amino group of the amidino-moiety is protected, e.g. by hydroxy or a (1–6C)alkoxycarbonyl group. Solvates according to the invention include hydrates The compounds of the invention, which can occur in the form of a free base, may be isolated from the reaction mixture in the form of a pharmaceutically acceptable salt. The pharmaceutically acceptable salts may also be obtained by treating the free base of formula (I) with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, ascorbic acid and the like.

The compounds of this invention possess chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the present invention can be prepared by first activating the carboxylate group of the NAPAP analogue of formula II and subsequently addition of a pentasaccharide-spacer residue containing an amine group (formula III), optionally followed by deprotection of the amidine moiety.

The carboxylate group in compounds of formula II can be activated as a mixed anhydride or more preferably as an activated ester such as the ester of N-hydroxysuccinimid. pentafluorophenol or 1-hydroxybenzotriazol. In the coupling step, the benzamidine group in formula II can be unprotected (R'=R"=H), or can optionally be protected using a carbamate group preferably allyloxycarbonyl (R' and/or R" is H₂C=CH—CH—C(O)O) or benzyloxycarbonyl (R' and/or R" is PhCH₂—C(O)O). The allyloxycarbonyl and benzyloxycarbonyl protecting groups can be removed under relative mild conditions. The allyloxycarbonyl group can be removed using Pd in the presence of a weak nucleophile such as morpholine or a malonic ester. The benzyloxycarbonyl group can be removed under conditions such as hydrogen/Pd(C). Alternatively, synthetic precursors of benzamidine such as N-alkoxybenzamidine or N-benzyloxybenzamidine (R'=H, R"=alkoxy or benzyloxy) can be applied. These synthetic precursors can be transformed into benzamidine using reductive conditions such as hydrogenation (e.g. Fujii, T et al. Chem. Pharm. Bull, 39, 301, 1991 and Fujii, T et al. Chem. Pharm. Bull, 42, 1231, 1994).

The preferred benzamidine precursor is 1,2,4-oxadiazolin-5-one (—R'—R"=—C(O)O—). This precursor can be converted into the benzamidine by hydrogenation (Bolton, R. E. et al, Tetrahedron Letters, Vol 36, No 25, 1995, pp 4471–4474). Compounds of formula II can be prepared in various ways using methods known in the art. A method to prepare compounds of formula II wherein R'=R"=H; n is 3 and m is 1 is described in EP 0513543. Compounds of formula II in which the amidine is protected, for instance with a allyloxycarbonyl or benzyloxycarbonyl group can be prepared from compounds of formula IV wherein the amidine is protected with a allyloxycarbonyl or benzyloxycarbonyl group using methods commonly known in the art for the coupling of peptide fragments. The carbamates of formula IV can for instance be prepared from the corresponding amidine (formula IV, R'=R"=H) as described in literature e.g. Weller, T et al. J. Med. Chem. 39, 3119, 1996).

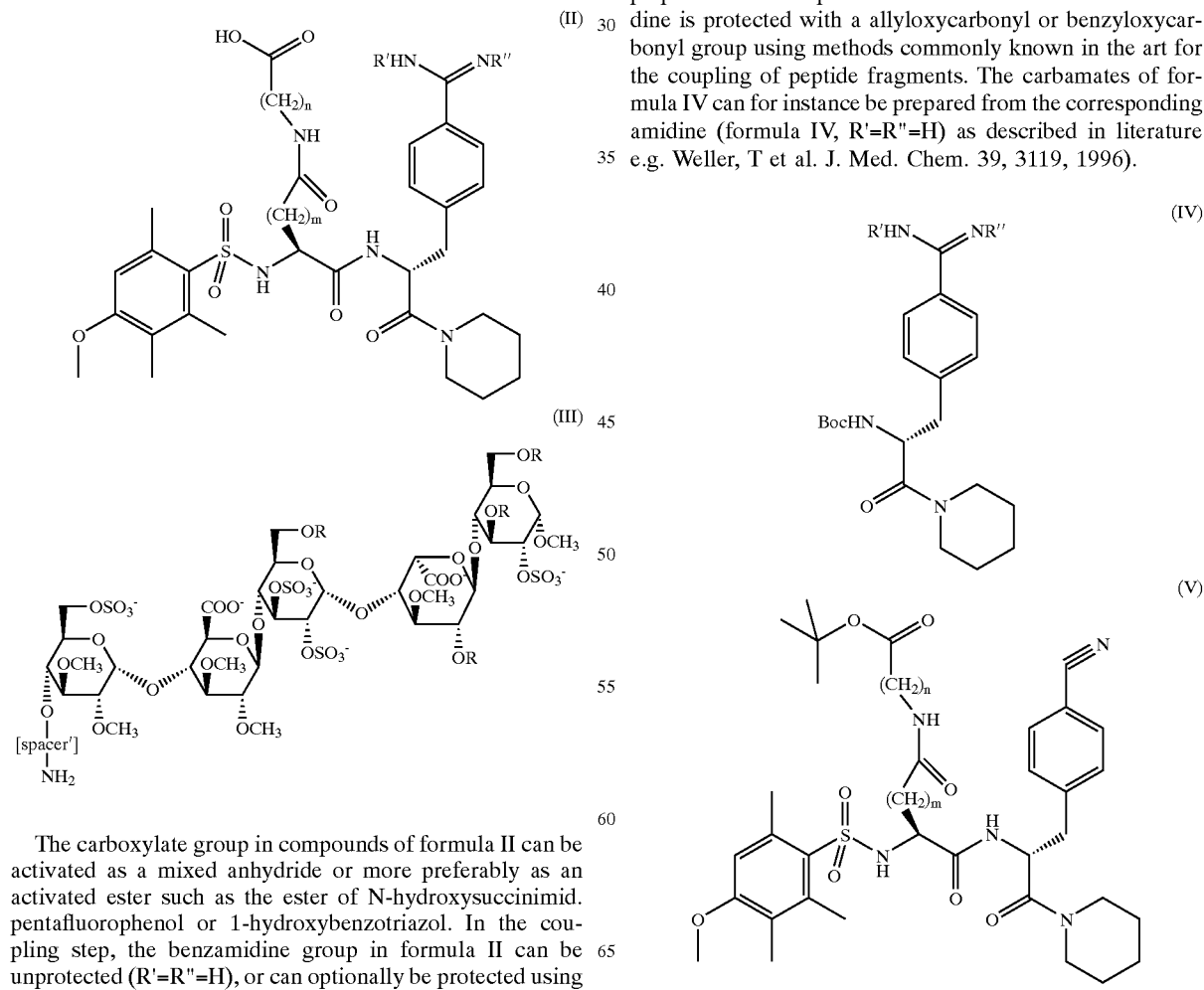

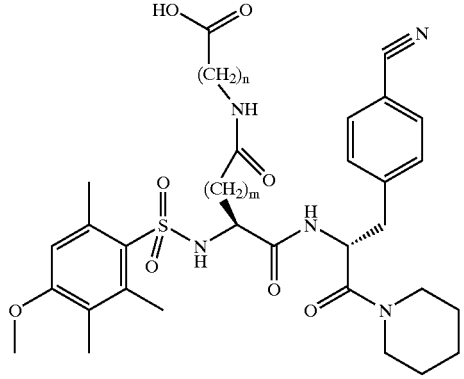
(VI)

The N-alkoxybenzamidine and N-benzyloxybenzamidine compounds of formula II can be prepared from compound V (described in EP 0513543) by treatment of this cyano compound with O-alkyl-hydroxylamine or O-benzyl-hydroxylamine followed by removal of the t-butyl ester using acidic conditions. Alternatively, the N-alkoxybenzamidine and N-benzyloxybenzamidine compounds of formula II can be prepared by first removal of the t-butyl ester of compound V using acidic conditions to yield compound VI and subsequently reaction of this cyano compound with O-alkyl-hydroxylamine or O-benzyl-hydroxylamine.

Compounds of formula II in which —R'—R"—=—C(O)O— (the 1,2,4-oxadiazolin-5-one group), can be prepared from compounds of formula IV in which —R'—R"—=—C(O)O—, using methods known in the art for coupling of peptide fragments.

The synthesis of amino-oligosacharide-spacer residues of formula III can for instance be performed by using methods described in EP 0649854. The saccharide residues of the compounds of the present invention may be prepared according to procedures known in the art, e.g. from WO 99/25720.

The peptide coupling, a procedural step in the above described method to prepare the compounds of the invention, can be carried out by methods commonly known in the art for the coupling—or condensation—of peptide fragments such as by the azide method, mixed anhydride method, activated ester method, or, preferably, by the carbodiimide method, especially with the addition of catalytic and racemisation suppressing compounds like N-hydroxysuccinimide and N-hydroxybenzotriazole. An overview is given in *The Peptides, Analysis Synthesis, Biology*, Vol 3, E. Gross and J. Meienhofer, eds. (Academic Press, New York, 1981) and Bodanszky, M.; Principles of peptide synthesis, Springer-Verlag, 1984.

Amine functions present in the compounds may be protected during the synthetic procedure by an N-protecting group, which means a group commonly used in peptide chemistry for the protection of an α-amino group, like the tert-butyloxycarbonyl (Boc) group, the benzyloxycarbonyl (Z) group, the 9-fluorenylmethyloxycarbonyl (Fmoc) group or the phthaloyl (Phth) group. Removal of the protecting groups can take place in different ways, depending on the nature of those protecting groups. Usually deprotection takes place under acidic conditions and in the presence of scavengers. An overview of amino protecting groups and methods for their removal is given in the above mentioned *The Peptides Analysis. Synthesis, Biology*, Vol 3, and further as described by Greene, T. W. and Wuts, P. G. M. in Protective groups in organic synthesis, John Wiley & Sons Inc. 1991.

The compounds of the invention may be administered enterally or parenterally. The exact dose and regimen of these compounds and compositions thereof will necessarily be dependent upon the needs of the individual subject to whom the medicament is being administered, the degree of affliction or need and the judgement of the medical practitioner. In general parenteral administration requires lower dosages than other methods of administration which are more dependent upon absorption. However, the daily dosages are for humans preferably 0.001–100 mg per kg body weight, more preferably 0.01–10 mg per kg body weight.

The medicament manufactured with the compounds of this invention may also be used as adjuvant in acute anticoagulant therapy. In such a case, the medicament is administered with other compounds useful in treating such disease states.

Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is farther illustrated by the following examples.

EXAMPLE 1

Abbreviations used:
Ac=acetyl
Bn=benzyl
DBU=1,8-diazabicyclo[5.4.0]undec-7-ene
DCC=dicyclohexylcarbodiimide
DMF=N,N-dimethylformamide
Su=succinimidyl
Me=methyl
TBTU=2-(1H-benzotriazol-1-yl)-1,1,3,3-tetramethyluronium tetrafluoroborate
TEA=triethylamine
TFA=trifluoroacetic acid
Z=benzyloxycarbonyl The numbers of the compounds refer to the compounds in schemes 1 to 7.

Compound 3

To a stirred solution of compound 1 (53.6 g, 143.6 mmol) (R. Roy; W. K. C. Park; Q. Wu; S-N. Wang, Tetrahedron Lett., 1995, 36(25), 4377–80) and compound 2 (27.9 g. 89.3 mmol) (S. J. Danishefsky; M. P. DeNinno; G. B. Philips; R. E. Zelle, Tetrahedron, EN, 1986, 42, 11, 2809–2819) in 930 mL DMF was added sodium hydride (7.7 g 60%-dispersion, 192.2 mmol) at 50° C. After 1 h the reaction mixture was heated to 120° C. After stirring for 5 minutes the reaction mixture was cooled to 40° C. and diluted with water and extracted three times with dichloro methane The combined organic layers were washed with water and concentrated in vacuo, yielding crude product 3 (54 g). TLC: Rf=0.23, ether 100%.

Compound 4

To a stirred solution of compound 3 (89.3 mmol) in 800 mL dry toluene and 800 mL acetic anhydride was added dropwise a cooled solution of 361.5 mL sulfuric acid in acetic anhydride (16.5 mL concentrated sulfuric acid and 345.0 mL acetic anhydride) at −30° C. After 2 h the reaction mixture was quenched with 240 mL TEA and stirred at room temperature. To the solution was added aqueous sodium hydrogen carbonate (5%) and the water layer was extracted three times with ethyl acetate. The combined organic layers were washed twice with water and concentrated in vacuo. This procedure was repeated, resulting in crude compound 4 (53 g). TLC: Rf=0.29, ether 100%.

Compound 5

To a stirred solution of compound 4 (89.3 mmol) and ethanethiol (11.1 mL, 150.3 mmol) in 370 mL dry toluene was added dropwise a solution of $BF_3$-etherate in toluene (23.9 mL $BF_3$-etherate and 190 mL toluene) at 0° C. After stirring for 16 h at room temperature the reaction mixture was quenched with TEA and aqueous sodium hydrogen carbonate and extracted three times with ethyl acetate. The combined organic layers were washed with water and concentrated in vacuo. The crude product was purified by column chromatography (toluene/ethyl acetate=1/1 to 0/1, v/v) giving compound 5 (21.4 g). TLC: Rf=0.31, toluene/ethyl acetate=4/6, v/v.

Compound 7

A solution of donor 5 (15.0 g, 30.3 mmol) and acceptor 6 (23.0 g, 30.3 mmol) (WO 99/25720) in dry ether/dichloromethane (232 mL, 3/1, v/v) was stirred for 30 minutes under a flow of nitrogen in the presence of activated molecular sieves 4 Å (7.6 g). Then a solution of 1,3-dibromo-5,5-dimethylhydation (5.5 g, 19.1 mmol) and triflic acid (0.49 mL, 5.6 mmol) in dioxane/dichloromethane (69.8 mL, 1/1, v/v) was added dropwise in 75 minutes to the reaction mixture at −20° C. After 30 minutes TEA (5 mL) was added to the reaction mixture, which was stirred for 10 minutes and then filtered. The filtrate was washed with aqueous sodium thiosulphate (10%) and aqueous sodium hydrogen carbonate (10%) and concentrated in vacuo. The product was purified by column chromatography (0 to 5% acetone in dichloromethane) giving compound 7 (19.6 g). TLC: Rf=0.1, ether/heptane=8/2, v/v.

Compound 8

To a stirred solution of compound 7 (19.5 g 16.4 mmol) in dry toluene/acetic anhydride (442 mL, 1/1, v/v) was added dropwise a cooled solution of 131.5 mL sulfuric acid in acetic anhydride (1.5 mL concentrated sulfuric acid and 120 mL acetic anhydride) at −26° C. After 75 minutes TEA (73.5 mL) was added at −20° C. The acetic anhydride was decomposed by adding gradually 330 mL water maintaining the temperature between 25° C. and 30° C. After stirring for 16 h the mixture was poured into 800 mL water and extracted twice with toluene. The combined organic layers were washed with water and concentrated in vacuo. The crude product was purified by column chromatography (toluene/ethyl acetate/ethanol=96/2/2, v/v/v) giving 8 as a white foam (13.2 g).

TLC: Rf=0.29, toluene/ethanol=9/1, v/v.

Compound 9

To a solution of compound 8 (13.2 g, 11.7 mmol) in dry toluene (66 mL) at 32° C. was added morpholine (4.1 mL, 46.9 mmol). After stirring for 42 h at 32° C. the reaction mixture was cooled to room temperature and aqueous hydrochloric acid (17.6 mL, 4N) was added. The mixture was diluted with water and extracted twice with ethyl acetate. The combined organic layers were washed twice with water, dried on sodium sulfate and concentrated in vacuo yielding crude compound 9 (12.6 g).

TLC: Rf=0.32, toluene/aceton=7/31, v/v.

Compound 12

To a solution of compound 9 (12.6 g, 11.6 mmol) in dichloromethane (114 mL) was added trichloroacetonitrile (3.5 mL, 34.9 mmol) and DBU (52.2 μL, 0.35 mmol). After stirring for 2 h at room temperature activated molecular sieves 4 Å (24 g) and acceptor 11 (8.9 g, 13.0 mmol) (WO 99/25720) in dichloromethane (45 mL) were added to the reaction mixture. After stirring for 30 minutes at room temperature, the mixture was cooled to −20° C. and a solution of trimethylsilyl trifluoromethanesulfonate (405 μL, 2.1 mmol) in dichloromethane (100 mL) was added dropwise. After stirring for 30 minutes sodium hydrogen carbonate was added at −20° C. and the reaction mixture was filtered. The filtrate was poured into aqueous sodium hydrogen carbonate and extracted three times with dichloromethane. The combined organic layers were washed twice with water and concentrated in vacuo. The product was purified by column chromatography (1: $SiO_2$: 0–10% acetone in ether; 2: $SiO_2$ toluene/acetone=85/15 to 80/20, v/v; 3: RP-18: water/acetonitrile=2/8 to 0/10, v/v) yielding pure compound 12 (8.9 g). TLC: Rf=0.37, toluene/acetone=7/3, v/v.

Compound 14

A suspension of compound 12 (8.9 g, 5.1 mmol) and 10% Pd/C (8.9 g) in 312 mL DMF and 45 mL water was stirred under a continuous stream of hydrogen. After 4.5 h the Pd/C catalyst was removed by filtration. The filtrate was concentrated to a volume of 400 mL and treated with 10% Pd/C (1.5 g) under a stream of hydrogen for 5.5 h. The catalyst was removed by filtration. To the filtrate (900 mL) was added aqueous sodium hydroxide (32 mL, 4N). After stirring for 4 h at room temperature the mixture was acidified to pH=6.6 with 1N hydrochloric acid and then concentrated in vacuo. The crude product was desalted on a Sephadex G-25 column which was eluted with water. The appropriate fractions were pooled and lyophilized yielding compound 14 (4.0 g).

Compound 15

Pentasaccharide 14 (700 mg, 0.61 mmol) was dissolved in water (13.2 mL) and DMF (3.3 mL) and treated with N-(benzyloxycarbonyloxy)-succinimide (224 mg, 0.90 mmol) and N-ethylmorpholine (233 μL, 1.83 mmol). After stirring for 15 minutes the reaction mixture was directly applied onto a RP-18 column, which was eluted with water/acetonitrile 10/0 to 7/3. The appropriate fractions were pooled and concentrated to a small volume and applied onto a Dowex 50 WX4-$H^+$ ion-exchange column in water. The eluate was concentrated in vacuo to yield pure 15 (482 mg).

Compound 16

To a solution of compound 15 (471 mg, 0.37 mmol) in DMF (4.7 mL) was added sulphur trioxide-pyridine complex (1.1 g, 6.6 mmol) and the mixture was stirred for 16 h at 30° C. The mixture was cooled to room temperature and added dropwise to a cooled 10% sodium hydrogen carbonate solution (16.7 mL, 19.9 mmol) and stirred for 1 h at room temperature. The mixture was concentrated to a small volume and applied onto a Sephadex G-25 column, which was eluted with water. The appropriate fractions were pooled and concentrated to a small volume, which was subsequently passed through a column of Dowex Na+ HCRW2 eluted with water. The eluate was concentrated and redissolved in 8.3 mL 0.2N hydrochloric acid and allowed to stand for 16 h at 4° C. The reaction mixture was neutralized with 8 mL 0.2N sodium hydroxide and desalted on a Sephadex G-25 column which was eluted with water. The appropriate fractions were pooled and concentrated in vacuo yielding pure compound 16 (840 mg).

Compound 17

A suspension of compound 16 (0.37 mmol) and 10% Pd/C (820 mg) in tert-butanol (85 mL) and water (79 mL) and a few drops of acetic acid was stirred under a continuous stream of hydrogen. After 3 h the Pd/C catalyst was removed by filtration and the filtrate was concentrated and lyophilized giving pure 17 (675 mg).

4-[[4-[[(1R)-1-[[4-(aminoiminomethyl)phenyl]methyl]-2-oxo-2-(1-piperidinyl)ethyl]amino]-3-[[(4-methoxy-2,3,6-trimethylphenyl)sulfonyl]amino]-1,4(S)-dioxobutyl]amino]-butanoic acid benzyl ester. hydrochloride (18)

To a solution of 4-[[(1R)-1[[4-(aminoiminomethyl)phenyl]methyl]-2-oxo-2-(1-piperidinyl)ethyl]amino]-3-[[(4-methoxy-2,3,6-trimethylphenyl)sulfonyl]amino]-4-oxo-(3S) butanoic acid hydrochloride (2.38 g, 3.96 mmol) (Tetrahedron 51, 12047–12068, 1995) and benzyl-(4-aminobutyric acid).benzenesulfonate (1.52 g, 3.96 mmol) (J. Am. Chem. Soc. 105, 5278–5284, 1983) in DMF (40 mL) under a nitrogen atmosphere was added N,N-diisopropylethylamine (0.689 mL, 3.96 mmol) and tetramethyl-benzotriazolyl uronium tetrafluoroborate (1.91 g, 5.94 mmol). The pH of the reaction mixture was maintained at 6 using N,N-diisopropylethylamine. The reaction mixture was stirred for 4 days at room temperature, concentrated, dissolved in ethyl acetate, washed with 5% sodium carbonate and 0.1 N hydrochloric acid, dried on magnesium sulfate and concentrated. The residue was dissolved in dry ethanol (5 mL), precipitated with dry diisopropyl ether, filtered, to yield 2.47 g of the title compound 18.

Rf =0.8, ethyl acetate/pyridine/acetic acid/water=88/31/18/7, v/v/v/v; Mass (ESI+): 777.4 [M+H]+

4-[[4-[[(1R)-1-[[4-(aminoiminomethyl)phenyl]methyl]-2-oxo-2-(1-piperidinyl)ethyl]amino]-3-[[(4-methoxy-2,3,6-trimethylphenyl)sulfonyl]amino]-1,4(S)-dioxobutyl]amino]-butanoic acid. hydrochloride (19)

A suspension of 18 (2.42 g, 3.11 mmol) and 10% Pd/C (400 mg) in methanol/water (40 mL, 3/1, v/v) was stirred under a continous stream of hydrogen. After 8 h the reaction mixture was filtered, the filtrate was concentrated and coevaporated three times with methanol/toluene (1/10, v/v). The residue was dissolved in dry ethanol (5 mL), precipitated with dry diethyl ether, filtered and dried. The residue was dissolved in water and directly charged onto a preparative HPLC DeltaPak RP-$C_8$ using a gradient elution system of 20% A/60% B/20% C to 20% A/14% B/66% C over 60 min at a flow rate of 40 mL/min (A: 0.5M phosphate buffer pH 2.1; B: water; C: acetonitrile/water=6/4). Yield 598 mg.

$R_t$=26.4 min. (3–10 min: 20–43% C+20% A; 10–50 min.: 43–66% C+2 (A: phosphate buffer pH 2.1; B: water; C: acetonitrile/water=6/4, v/v), analytical HPLC supelcosil LC-18-DB; Mass (ESI+): 687.2 [M+H]+, (ESI−): 685.2 [M−H]

Compound 21 from Compound 17 and Compound 19

To a solution of compound 19 (40 mg, 58.3 μmol) in DMF (800 μL) was added N-hydroxysuccinimide (9.0 mg, 78.1 μmol), DCC (18.5 mg, 89.7 μmol) and 1-hydroxybenzotriazol (8.8 mg, 65.1 μmol). The reaction mixture was stirred for 40 h at room temperature. The reaction mixture was filtered over dicalite and the dicalite was washed four times with DMF (284 μL). To the filtrate was added 0.1M $Na_2HPO_4$ buffer (1936 μL, pH=7.5) and pentasaccharide 17 (94.7 mg, 52.6 μmol). After stirring for 30 minutes the mixture was filtered over dicalite, concentrated and applied onto a Sephadex G-50 column, which was eluted with acetonitrile/water (1/1, v/v). The appropriate fractions were pooled, concentrated and desalted twice by Sephadex G-50 column chromatography (water). The appropriate fractions were pooled and lyophilized yielding conjugate 21 as a white solid (95.8 mg). Mass (ESI+)=2469, HPLC: Rt=8.3 min (20–80% B in 15 minutes, A=water/acetonitrile 8/2; B=2M NaCl/acetonitrile 8/2, v/v), analytical HPLC MonoQ HR 5

Compound 22

A solution of (R)-N-Boc(4-cyanophenyl)alanine (25.0 g, 86.1 mmol), piperidine (21.3 mL, 215.3 mmol) and TBTU (41.5 g, 129.2 mmol) in dry $CH_2Cl_2$ (500 mL) was stirred at room temperature under a flow of nitrogen for 2 hours. The reaction mixture was washed successively with 0.2N hydrochloric acid, water, aqueous sodium hydrogen carbonate (saturated) and water. The organic layer was dried on $MgSO_4$, filtered and concentrated in vacuo. The product was dissolved in hot ethyl acetate (35 mL), precipitated with heptane (190 mL) and filtered to yield compound 22 (27.75 g).

TLC: Rf=0.58, heptane/ethyl acetate=3/7, v/v.

Compound 23

A solution of compound 22 (25.6 g, 71.7 mmol), hydroxylamine HCl (7.1 g, 101.8 mmol) and triethylamine (16.8 mL, 120.5 mmol) in absolute ethanol (307 mL) was stirred at 80° C. for 4 hours. Upon cooling the mixture to room temperature crystals were formed. The crystals were filtered off, washed with ethanol and ether and dried in a desiccator to yield compound 23 (24.5 g).

TLC: Rf=0.15, heptane/ethyl acetate=3/7, v/v.

Compound 24

A solution of compound 23 (24.5 g, 62.7 mmol) and ethyl chloroformate (7.2 mL, 75.3 mmol) in dry pyridine (245 mL) was stirred at 115° C. for 2 hours. The reaction mixture was cooled to room temperature and poured into water (1250 mL) and extracted 3 times with ethyl acetate (500 mL). The combined organic extract was dried on $MgSO_4$, filtered and concentrated in vacuo to yield compound 24 (24.3 g).

TLC: Rf=0.42, $CH_2Cl_2$/MeOH 95/5, v/v.

Compound 25

A solution of compound 24 (24.3 g, 58.4 mmol) in dry $CH_2Cl_2$ (122 mL) and TFA (122 mL) was stirred at room temperature for 2 hours and concentrated in vacuo in the presence of toluene to yield compound 25 (37.6 g).

TLC: Rf=0.35, $CH_2Cl_2$/MeOH 8/2, v/v.

Compound 26

A suspension of H-Asp-(OtBu)-OH (39 g, 206.35 mmol), 4-methoxy-2,3,6-trimethylbenzene-sulfonyl chloride (62 g, 249.3 mmol) and diisopropylamine (89 mL, 635 mmol) in DMF (950 mL) and water (450 mL) was stirred at 0° C. for 3 hours. The reaction mixture was poured into ice/water (5 L) and washed twice with diethyl ether, acidified with aqueous hydrochloric acid (4N, 72 ml) and extracted 3 times with ethyl acetate. The combined ethyl acetate layers were dried on $MgSO_4$, filtered and concentrated in vacuo to yield compound 26 (97.7 g).

TLC: Rf=0.67, $CH_2Cl_2$/MeOH 8/2, v/v.

Compound 27

A solution of compound 25 (33.5 g), compound 26 (24.7 g), TBTU (36.8 g, 114.6 mmol) and diisopropylamine (27.2 mL, 194.1 mmol) in dry DMF (670 mL) was stirred for 2 hours and concentrated in vacuo. The residue was dissolved in ethyl acetate (750 mL), washed with aqueous sodium hydrogen carbonate (5%, 1250 mL) and aqueous hydrochloric acid (0.1N, 1250 mL), dried on $MgSO_4$, filtered and concentrated in vacuo to yield compound 27 (33.8 g).

TLC: Rf=0.88, $CH_2Cl_2$/MeOH 8/2, v/v.

Compound 28

A solution of compound 27 (33.8 g, 48.3 mmol) in dry $CH_2Cl_2$ (170 mL) and TFA (170 mL) was stirred at room temperature for 2 hours and concentrated in vacuo in the presence of toluene to yield compound 28 (32.3 ).

TLC: Rf=0.73, $CH_2Cl_2$/MeOH 8/2. v/v.

Compound 29

A solution of compound 28 (32.3 g). H-GABA-OtBu.HCl (9.5 g, 48.4 mmol), TBTU (29.0 g, 90.5 mmol) and diisopropylamine (25.2 mL, 179.8 mmol) in dry DMF (622 mL) was stirred at room temperature for 2 hours and concentrated in vacuo. The residue was dissolved in ethyl acetate (840 mL), washed with aqueous sodium hydrogen carbonate (5%, 1400 mL) and aqueous hydrochloric acid (0.1N, 1400 mL), dried on $MgSO_4$, filtered and concentrated in vacuo. The residue was dissolved in ethanol (75 mL) and slowly added to stirred diisopropylether (2990 mL) yielding the compound 29 as off-white crystals (32.0 g).

TLC: Rf=0.56, $CH_2Cl_2$/MeOH 9/1, v/v.

Compound 30

A solution of compound 29 (3.0 g, 3.82 mmol) in dry $CH_2Cl_2$ (15 mL) and TFA (15 mL) was stirred at room temperature for 2 hours and concentrated in vacuo in the presence of toluene. The residue was purified on silica gel using $CH_2Cl_2$/MeOH (0%-6% MeOH) yielding the pure compound 30 (1.98 g).

TLC: Rf=0.56, $CH_2Cl_2$/MeOH 8/2, v/v.

Compound 31

A solution of compound 30 (900 mg, 1.23 mmol), TBTU (396 mg, 1.23 mmol) and diisopropylamine (215 μL, 1.53 mmol) in DMF (45 mL) was stirred for 2 hours at room temperature. Compound 17 (2.0 g, 1.11 mmol) was added and after stirring for 4 hours the mixture was concentrated in vacuo yielding the compound 31 (4.17 g).

Compound 21 from Compound 31

A suspension of compound 31 (4.17 g) and 10% Pd/C (2.8 g) in tert-butyl alcohol (28 mL) and water (56 mL) was stirred overnight under a continuous stream of hydrogen. The Pd/C catalyst was removed by filtration and the filtrate was concentrated in vacuo. The residue was dissolved in water and purified on a Q-sepharose column. The appropriate fractions were pooled, concentrated and desalted by Sephadex G-25 column chromatography (water). The appropriate fractions were pooled and lyophilized yielding the conjugate 21 as a white solid (1.74 g).

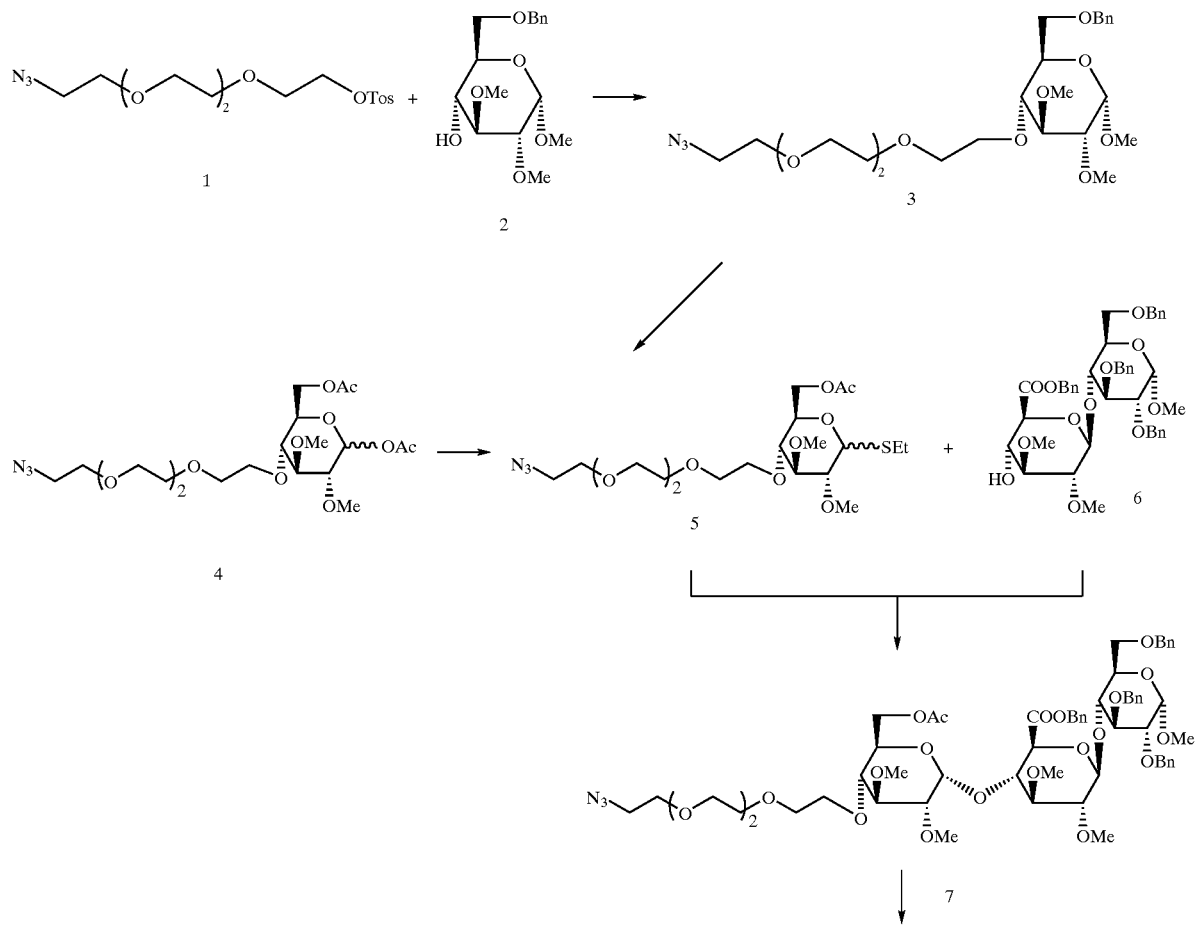

Scheme 1

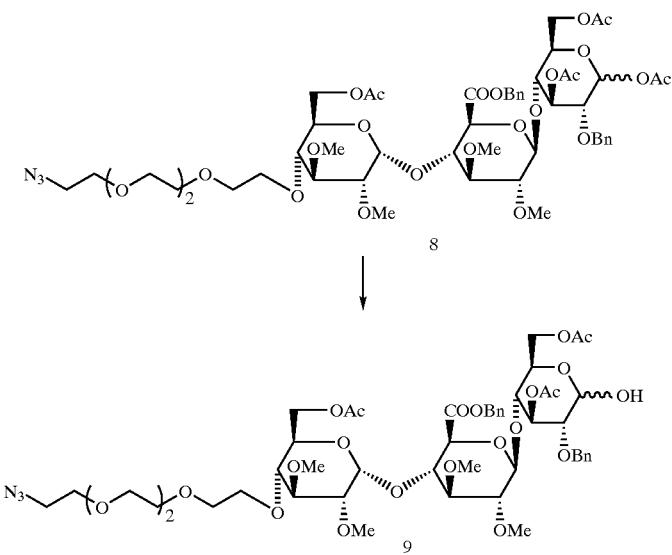
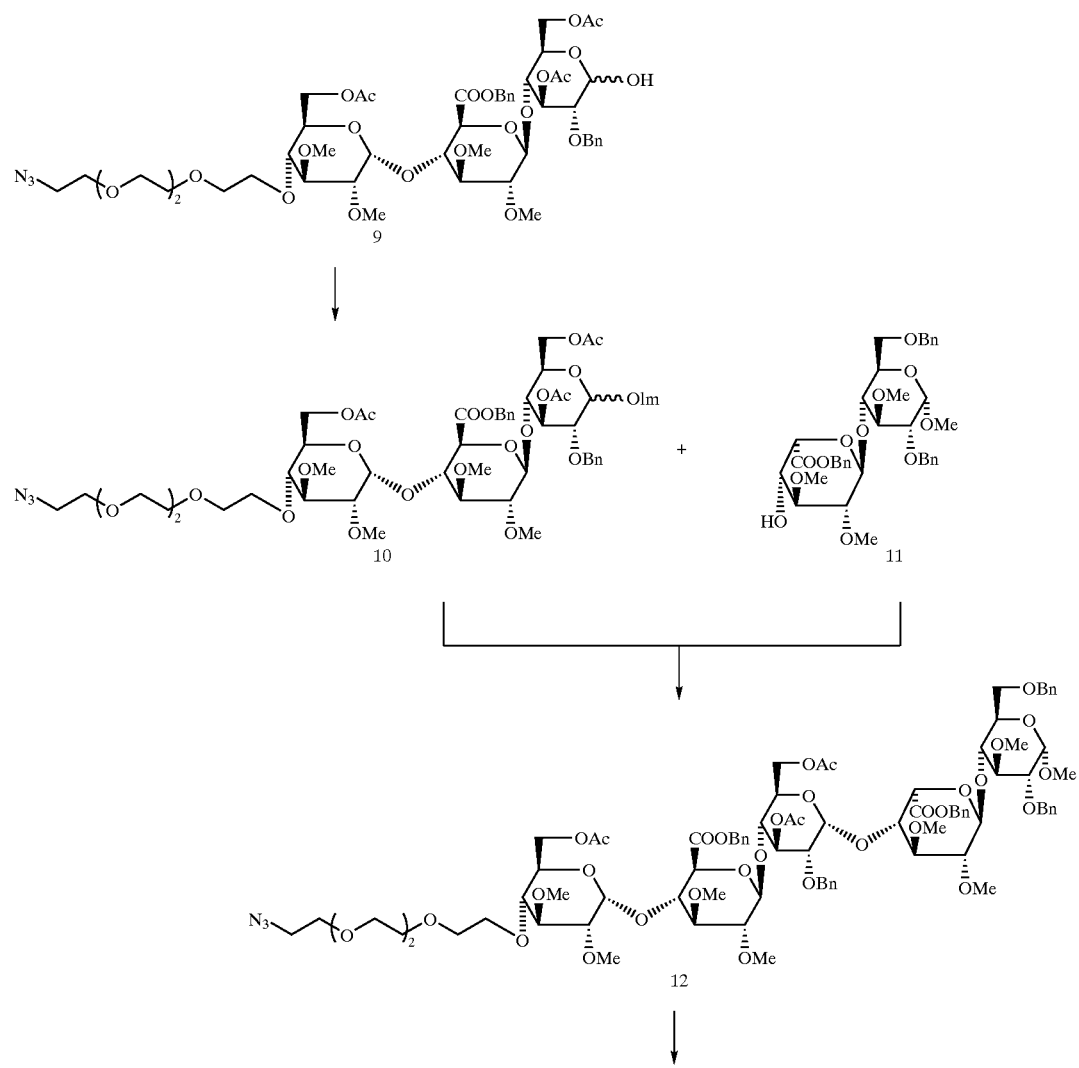

-continued
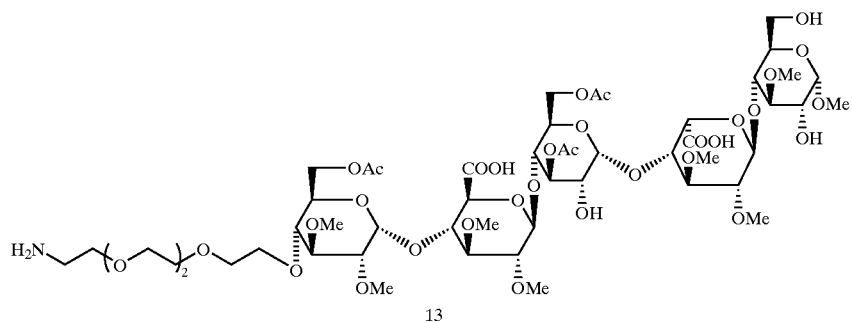
Scheme 3
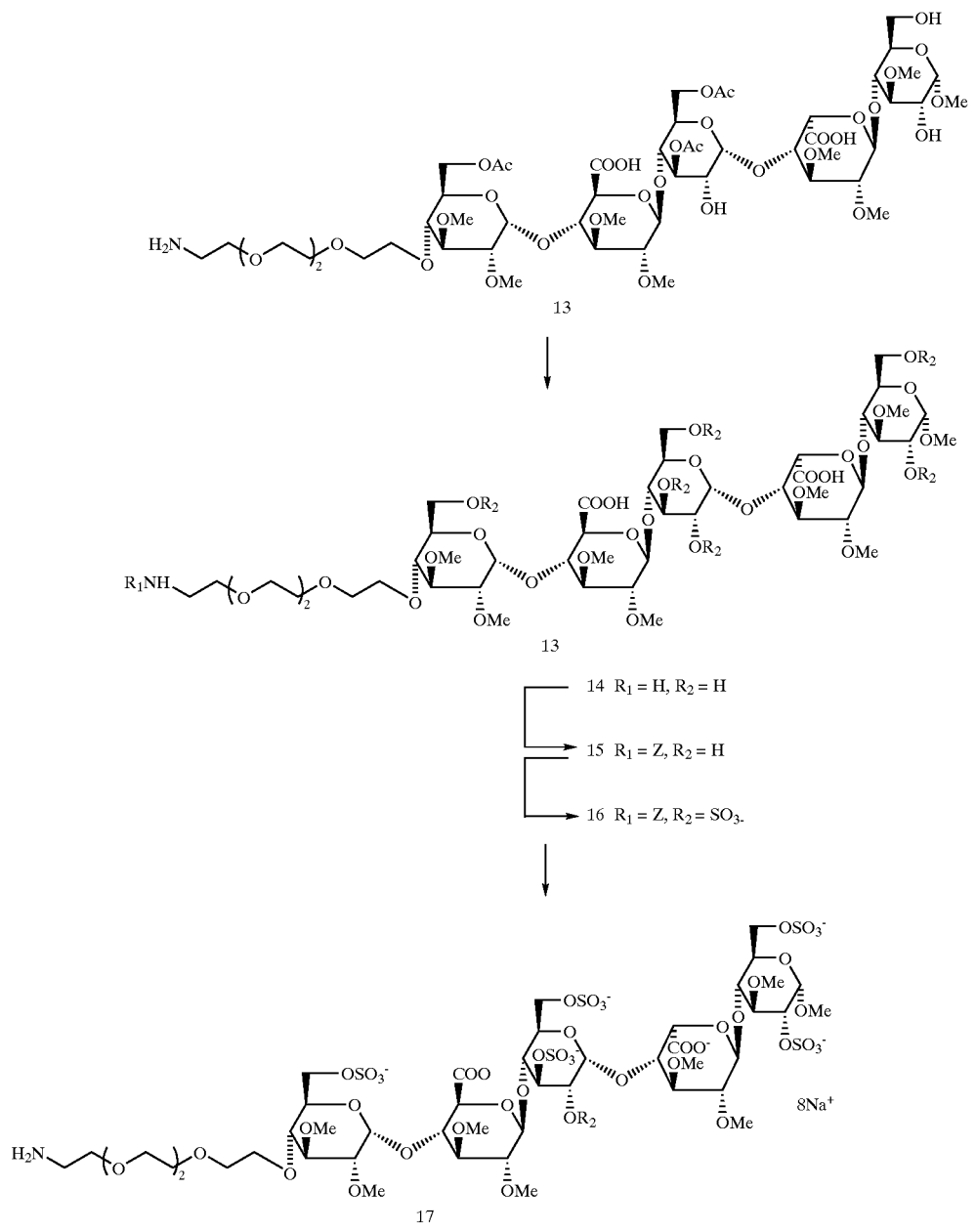

Scheme 4
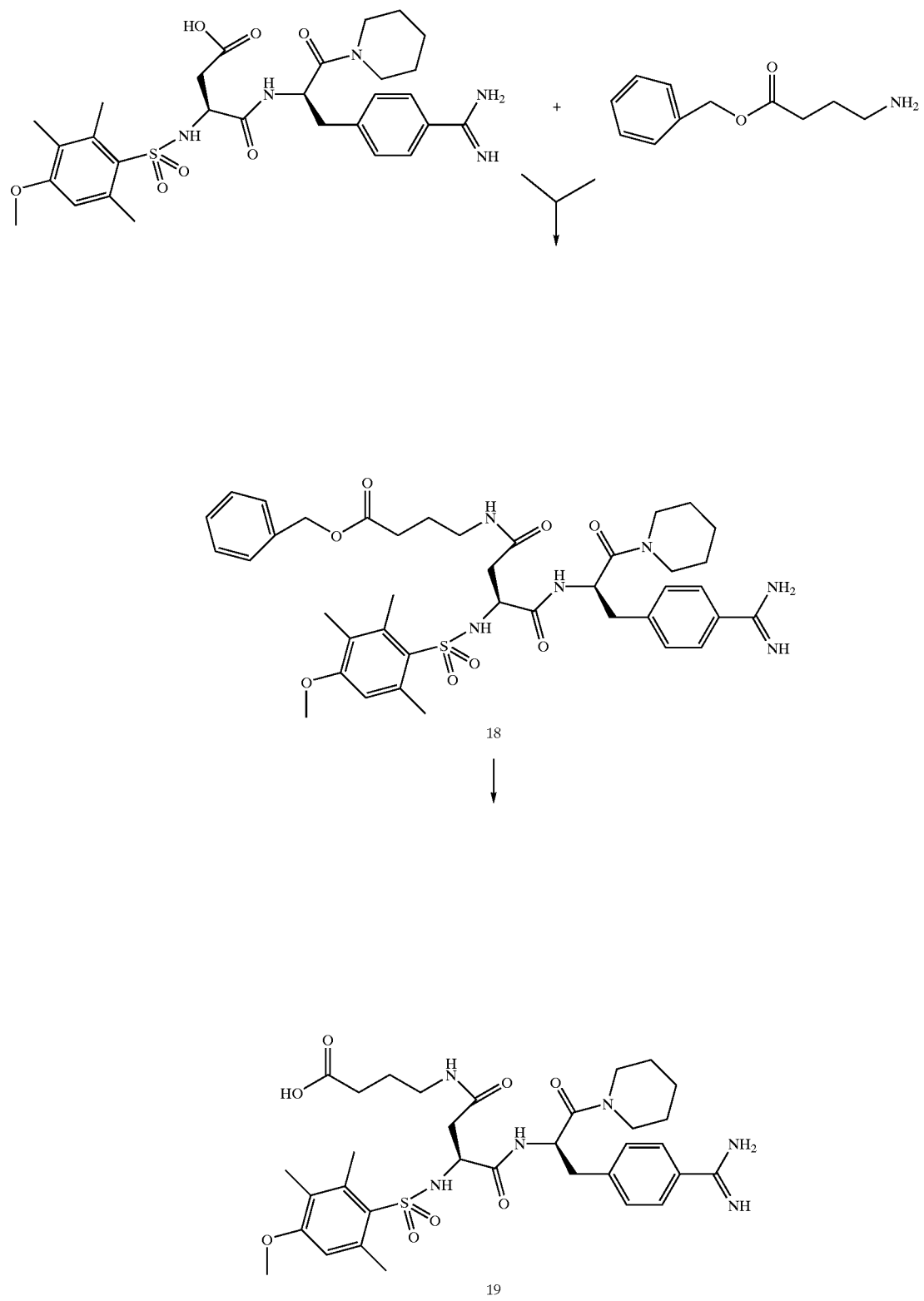

Scheme 5
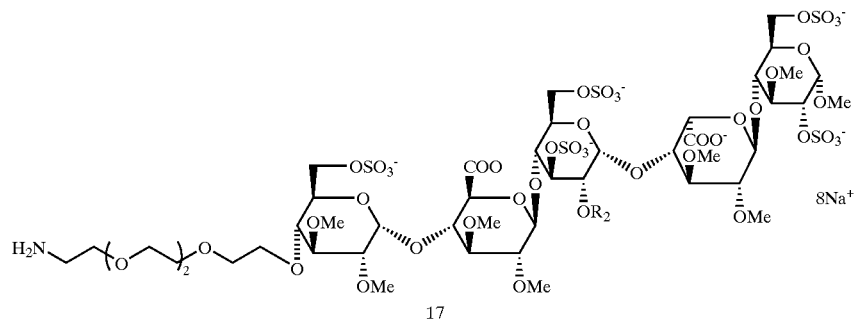
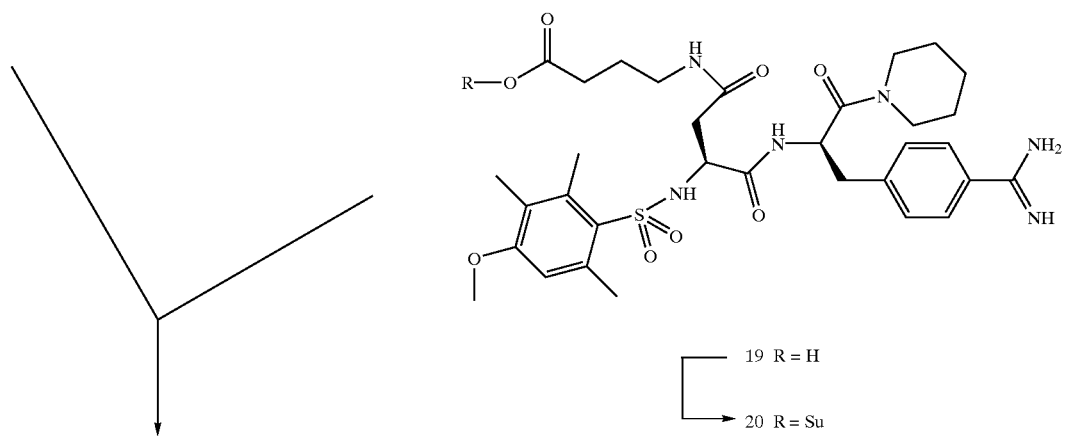
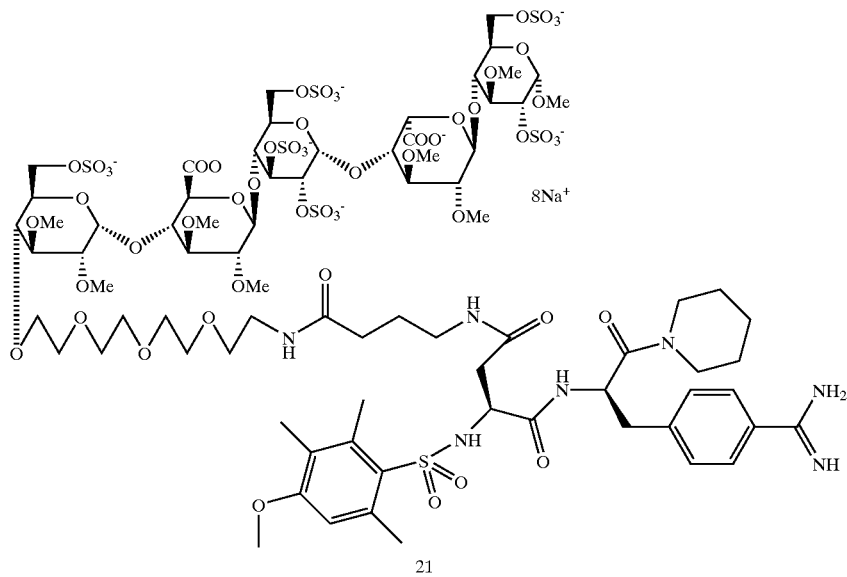

Scheme 6
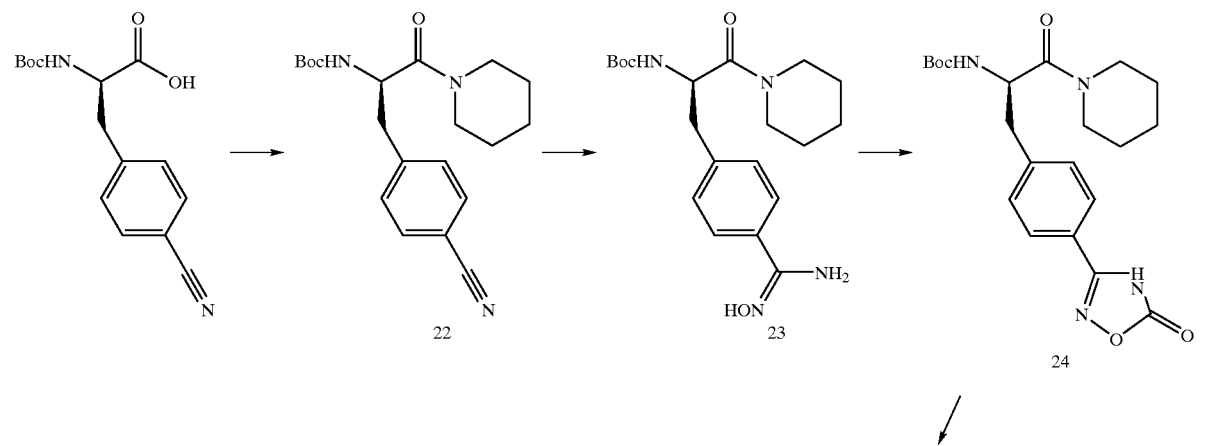
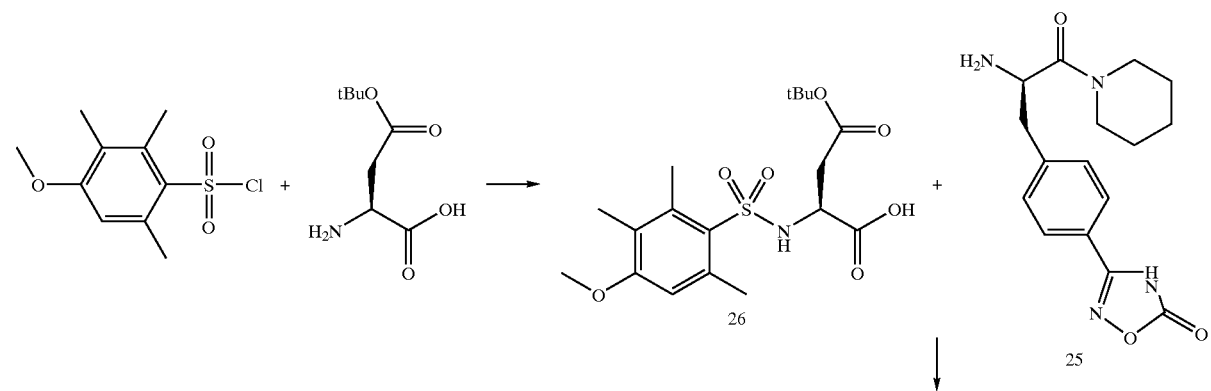
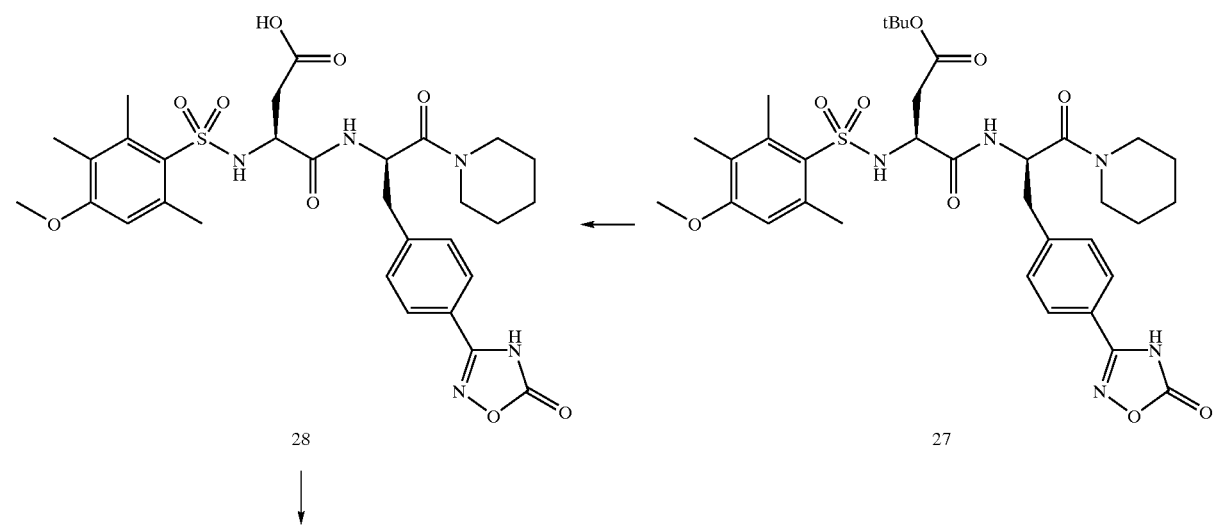

25
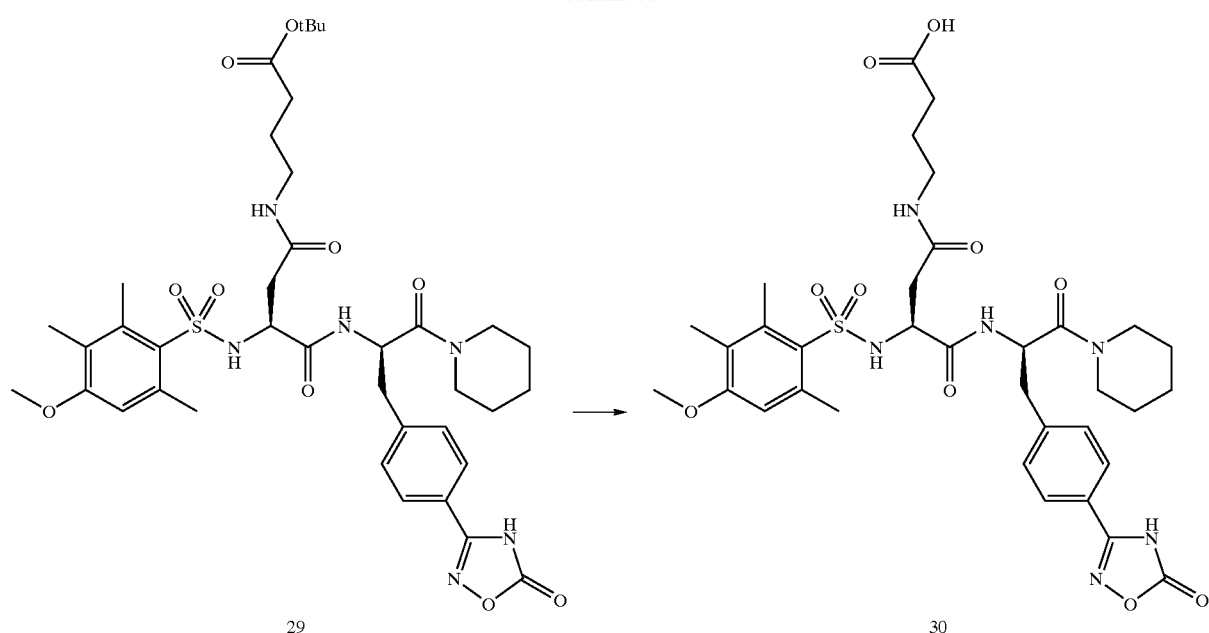
-continued
26
Scheme 7
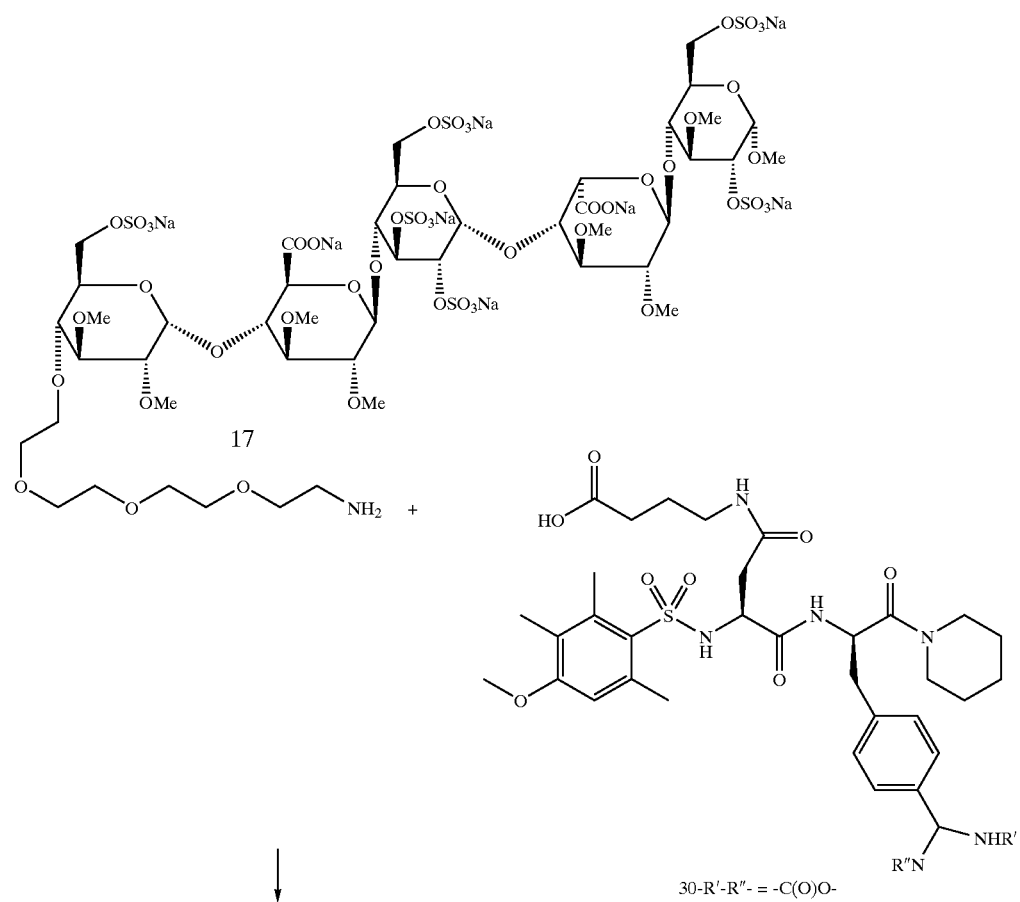

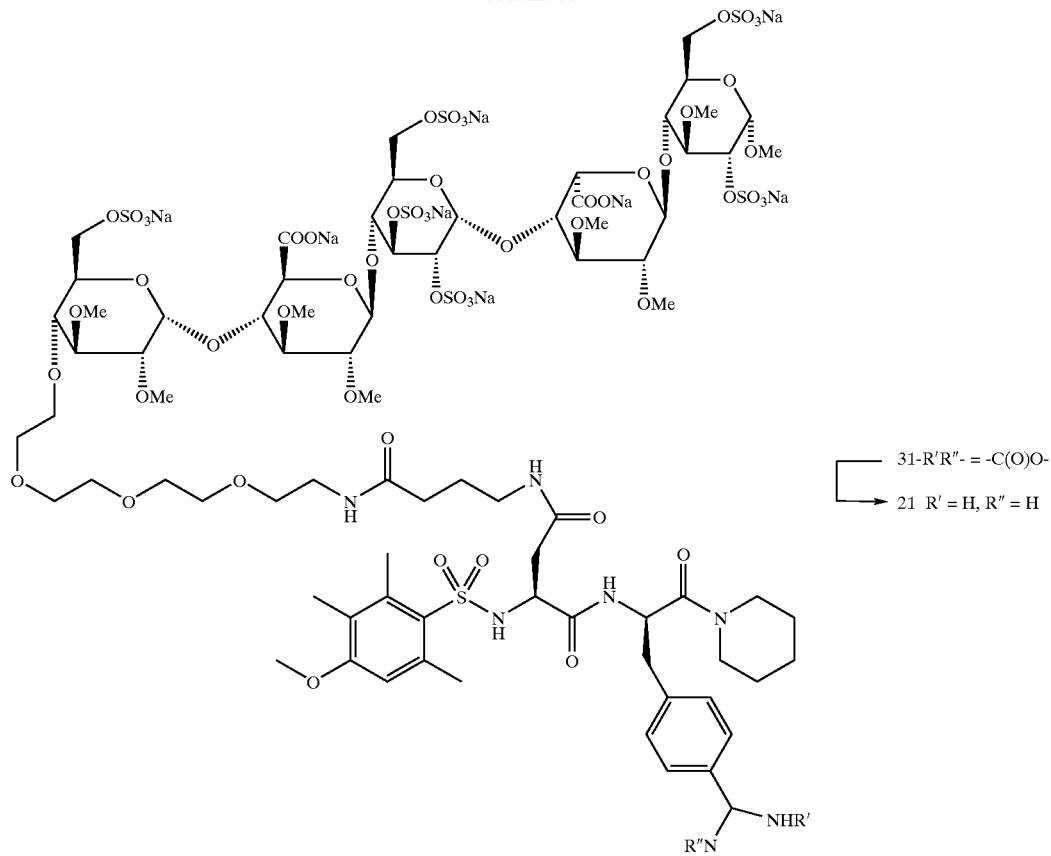

EXAMPLE 2

The biological activities of compounds of the present invention are determined by the following test methods.

I. Anti-Thrombin Assay

Thrombin (Factor IIa) is a factor in the coagulation cascade.

The anti-thrombin activity of compounds of the present invention was assessed by measuring spectrophotometrically the rate of hydrolysis of the chromogenic substrate s-2238 exterted by thrombin. This assay for anti-thrombin activity in a buffer system was used to assess the $IC_{50}$-value of a test compound.

Test medium: Tromethamine-NaCl-polyethylene glycol 6000 (TNP) buffer

Reference compound: 12581 (Kabi)

Vehicle: TNP buffer.

Solubilisation can be assisted with dimethylsulphoxide, methanol, ethanol, acetonitrile or tert.-butyl alcohol which are without adverse effects in concentrations up to 2.5% in the final reaction mixture.

Technique:

Reagents* 1.Tromethamine-NaCl (TN) buffer; composition of the buffer: Tromethamine (Tris) 6.057 g (50 mmol), NaCl 5.844 g (100 mmol), Water to 1 l. The pH of the solution is adjusted to 7.4 at 37° C. with HCl (10 mmol·l$^{-1}$).
2. TNP buffer: Polyethylene glycol 6000 is dissolved in TN buffer to give a concentration of 3 g·l$^{-1}$ 3. S-2238 solution: One vial S-2238 (25 mg Chromogenix; Sweden) is dissolved in 20 ml TN buffer to give a concentration of 1.25 mg·ml$^{-1}$ (2 mmol·l$^{-1}$). 4. Thrombin solution: Human thrombin (1000 NIH units/vial, Enzyme Res. Lab. Inc., USA) is dissolved in TNP buffer to give a stock solution of 50 NIH units.ml$^{-1}$. Immediately before use this solution is diluted with TNP buffer to give a concentration of 30.2 NIH units.ml$^{-1}$.

All ingredients used are of analytical grade

For aqueous solutions ultrapure water (Milli-Q quality) is used.

Preparation of Test and Reference Compound Solutions

The test and reference compounds are dissolved in Milli-Q water to give stock concentrations of $10^{-2}$ mol·l$^{-1}$. Each concentration is stepwise diluted with the vehicle to give concentrations of $10^{-3}$, $10^{-4}$ and $10^{-5}$ mol·l$^{-1}$. The dilutions, including the stock solution, are used in the assay (final concentrations in the reaction mixture: $3·10^{-4}$; $10^{-4}$; $3·10^{-5}$; $10^{-5}$; $3·10^{-6}$; $10^{-6}$ $3·10^{-7}$ and $10^{-7}$ mol·l$^{-1}$, respectively).

Procedure

At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2238 solution is added to each well and the plate is pre-heated and pre-incubated with shaking in an incubator (Amersham) for 10 min. at 37° C. Following pre-incubation the hydrolysis of S-2238 is started by addition of 0.030 ml thrombin solution to each well. The plate is incubated (with shaking for 30 s) at 37° C. Starting after 1 min of incubation, the absorbance of each sample at 405 nm is measured every 2 min for a period of 90 min using a kinetic microtiter plate reader (Twinreader plus, Flow Laboratories).

All data are collected in a personal computer using a data processing program (Biolise). For each compound concentration (expressed in mol·l$^{-1}$ reaction mixture) and for the blank the absorbance is plotted versus the reaction time in min.

Evaluation of Responses: For each final concentration the maximum absorbance was calculated from the assay plot. The IC$_{50}$-value (final concentration, expressed in μmol·l$^{-1}$, causing 50% inhibition of the maximum absorbance of the blank) was calculated using the logit transformation analysis according to Hafner et al. (Arzneim.-Forsch./Drug Res. 1977; 27(II): 1871–3).

Antithrombin activity of the compound of EXAMPLE 1: IC$_{50}$-value: 17 nM

II. Anti-Factor Xa Assay

Activated Factor X (Xa) is a factor in the coagulation cascade. The anti-Xa activity of compounds of the present invention was assessed by measuring spectrophotometrically the rate of hydrolysis of the chromogenic substrate s-2222 exterted by Xa. This assay for anti-Xa activity in a buffer system was used to assess the IC$_{50}$-value of the test compound.

Reference compound: pentasaccharide Org 31540
Vehicle: TNP buffer.

Solubilisation can be assisted with dimethylsulphoxide, methanol, ethanol, acetonitrile or tert.-butyl alcohol which are without adverse effects in concentrations up to 1% (for DMSO) and 2.5% (for the other solvents) in the final reaction mixture.

Technique

Reagents* 1.Tromethamine-NaCl (TN) buffer; composition of the buffer: Tromethamine (Tris) 6.11 g (50.4 mmol), NaCl 10.17 g (174 mmol), Polyethylene glycol 6000 3 g·l$^{-1}$, Water to 1 l. The pH of the solution is adjusted to 7.4 at 37° C. with HCl (10 mmol·l$^{-1}$): 3. S-2222 solution: one vial S-2222 (25 mg; Chromogenix, Sweden) is dissolved in water to give a concentration of 0.375 mg·ml$^{-1}$ (0.5 mmol·l$^{-1}$). 4. Xa solution: Bovine Factor Xa Human (71 nKat·vial$^{-1}$; Chromogenix) is dissolved in 10 ml TNP buffer and then, further diluted with TNP buffer to give a concentration of 0.75 nKat·(1.5 U).ml$^{-1}$. The dilution has to be freshly prepared. 5. ATIII solution: Human ATIII (Chromogenix) is disssolved in water to give a concentration of 1 U.ml$^{-1}$, after which the solution is further diluted with 3 volumes of TNP buffer to a concentration of 0.25 U.ml$^{-1}$.6 Standard solution: a stock solution of 5.7 anti-Xa U.ml$^{-1}$ Org 31540 was diluted in TNP buffer to 0.05 U.ml$^{-1}$. 6 Test samples: Each preparation is dissolved in water and diluted with TNP buffer to a concentration of 0.05 nmol.ml$^{-1}$. Of each preparation, a range of 9 dilutions were made (dilution factor 1.5).

Determination of the Xa Activity

Each test sample (0.05 ml) is pipetted into a well of a microtiter plate at room temperature. AT-Ill solution (0.05 ml) is added to each sample and the plate is shaken using a Vari-shaker. An aliquot of X$_a$ solution (0.05 ml) is pipetted into each well 10 min following addition of AT-III solution and the plate is shaken again. Exactly 2 min following addition of X$_a$ solution, 0.1 ml S-2222 solution is pipetted into each well and the plate is shaken again. For all additions a 12-channel pipette is used. The remaining amount of X$_a$ catalyses the hydrolysis of S-2222, the rate of which is measured photometrically following incubation periods of 2 and 22 min respectively at room temperature. The absorbance of each sample is measured at 405 nm using a Reader Microelisa, model 310C (Organon Teknika, Oss, The Netherlands) and the increase in absorbance (ΔOD) is calculated. Each test sample is determined in duplicate. With every 10 samples, a blank (0.05 ml TNP buffer) is included.

Calibration Curve

From an aliquot of the standard solution of the calibration sample a range of dilutions is made (dilution factor 1.4 for Org 31540 samples). The resulting standard samples (approx. 12 samples) should contain between 0.01–0.05 anti-X$_a$ U/ml. Within each run, 0.05 ml of each standard sample is tested at least 3 times as described under "Determination of X$_a$ activity". A calibration curve is obtained by fitting a straight line to $$\log \frac{\text{mean }\Delta OD(\text{blank}) - \text{mean }\Delta OD(\text{standard sample})}{\text{mean }\Delta OD(\text{standard sample})} \text{ against log anti-Xa}$$

U/ml values, using the method of least squares.

Evaluation of Responses: For each sample the mean anti-X$_a$ activity in U/ml is determined using the calibration curve.

Anti-factor Xa activity of the compound of EXAMPLE 1: 1012 U/μmol

What is claimed is:

1. A compound of the formula (I)

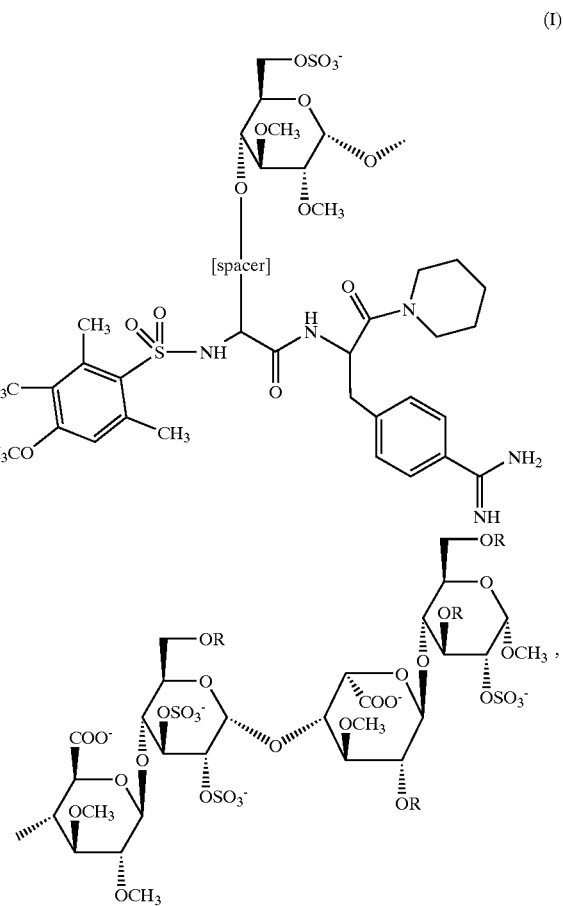

wherein R is independently SO$_3^-$ or CH$_3$;
the spacer is represented by *—(CH$_2$CH$_2$O)$_p$—(CH$_2$)—NH—C(O)—(CH$_2$)$_n$—NH—C(O)—(CH$_2$)$_m$—, wherein * indicates the end attached to the pentacaccharide residue,
p is 1–5,
n is 1–5 and
m is 1 or 2;
the charge of the pentasaccharide residue is compensated by positively charged counterions; and and the total number of sulfate groups in the pentasaccharide residue is 4, 5 or 6;

or a pharmaceutically acceptable salt, a prodrug or solvate thereof.

2. The compound of claim 1, wherein the pentasaccharide residue has the structure

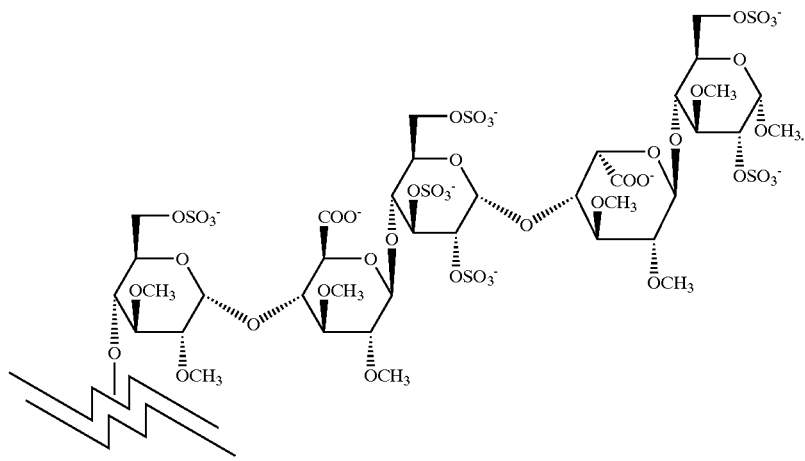

3. The compound of claim 1, wherein the spacer is *—(CH$_2$CH$_2$O)$_3$—(CH$_2$)$_2$—NH—C(O)—(CH$_2$)$_3$—NH—C(O)—CH$_2$—, the indicated with * being attached to the pentasaccharide residue.

4. The compound of claim 1 having the structure

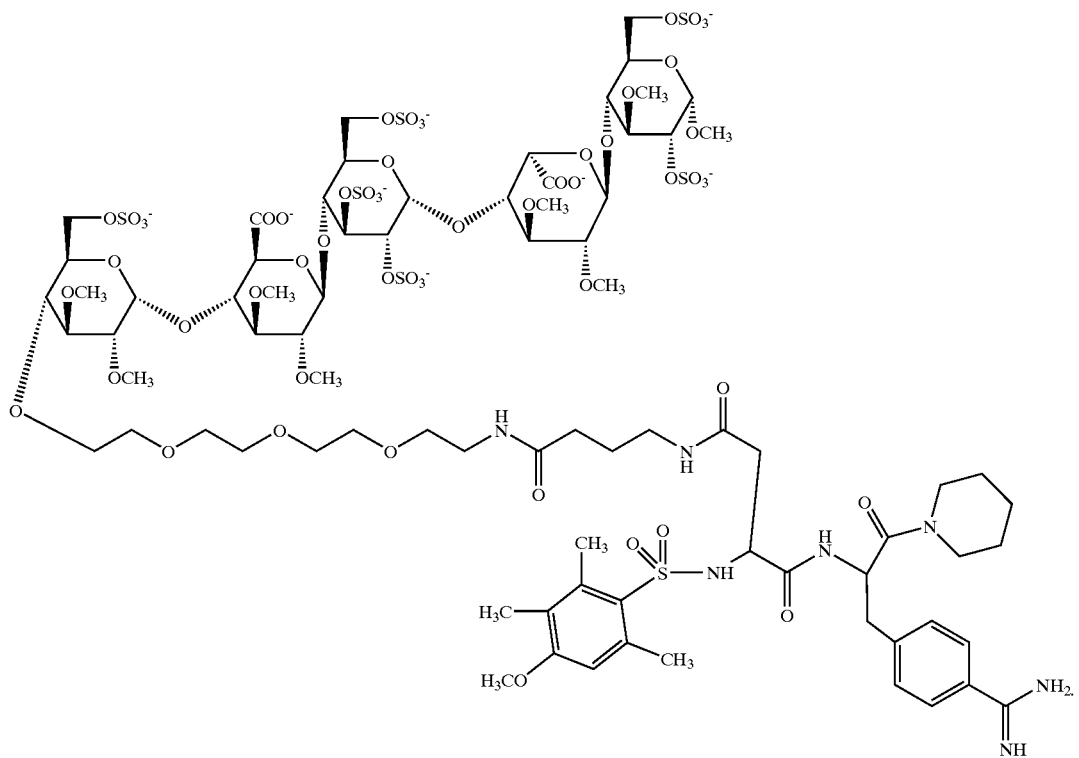

5. A process for the preparation of formula I,

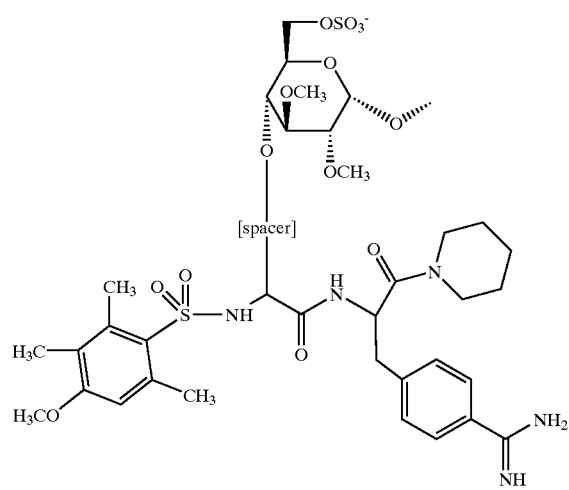

(I)

and the total number of sulfate groups in the pentasaccharide residue is 4, 5 or 6 comprising:
reacting an intermediate compound containing a benzamidine moiety precursor, said benzamidine moiety precursor represented by formula (II)

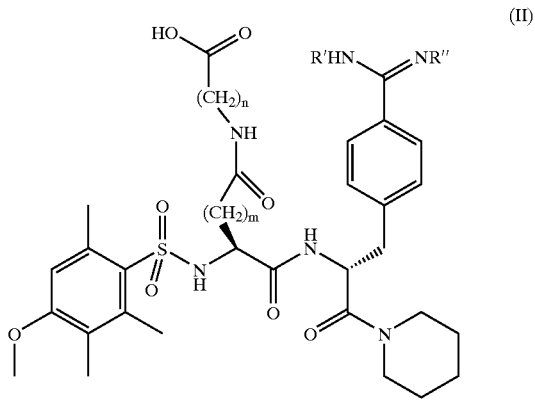

(II)

wherein R'—R"— —C(O)O—;
with a pentasaccharide containing reactant represented by formula (IIIa)

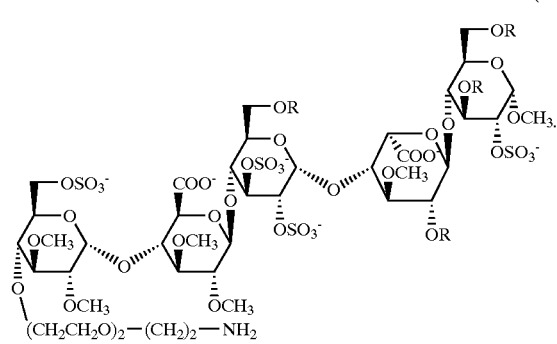

(IIIa)

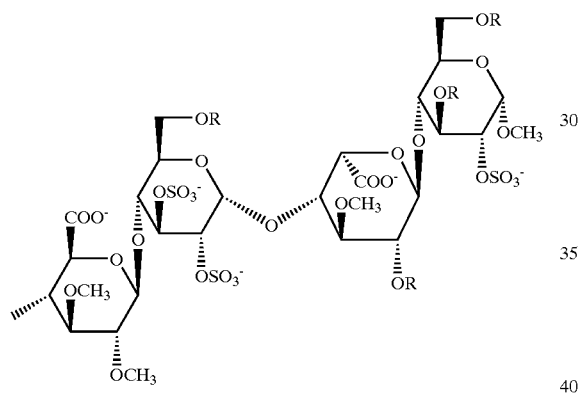

wherein R is independently $SO_3^-$ or $CH_3$;
the spacer is represented by *—$(CH_2CH_2O)_p$—$(CH_2)$—NH—C(O)—$(CH_2)_n$—NH—C(O)—$(CH_2)_m$—,
wherein * indicates the end attached to the pentacaccharide residue,
p is 1–5,
n is 1–5 and
m is 1 or 2;
the charge of the pentasaccharide residue is compensated by positively charged counterions; and 6. A pharmaceutical composition, comprising:
the compound of claim 1 and
pharmaceutically suitable auxiliaries.

7. A method of treating thrombosis of thrombosis-related diseases in a patient, comprising:
administering an effective amount to said patient of the compound according to claim 1 and
pharmaceutically suitable auxiliaries.

8. The compound of claim 1, wherein p=3.

* * * * *

UNITED STATES PATENT AND TRADEMARK OFFICE
CERTIFICATE OF CORRECTION

PATENT NO. : 6,875,755 B2
APPLICATION NO. : 10/148868
DATED : April 5, 2005
INVENTOR(S) : Van Boeckel et al.

It is certified that error appears in the above-identified patent and that said Letters Patent is hereby corrected as shown below:

Col. 17, 18, 21 and 22 scheme 3 structure of structure 17, should read

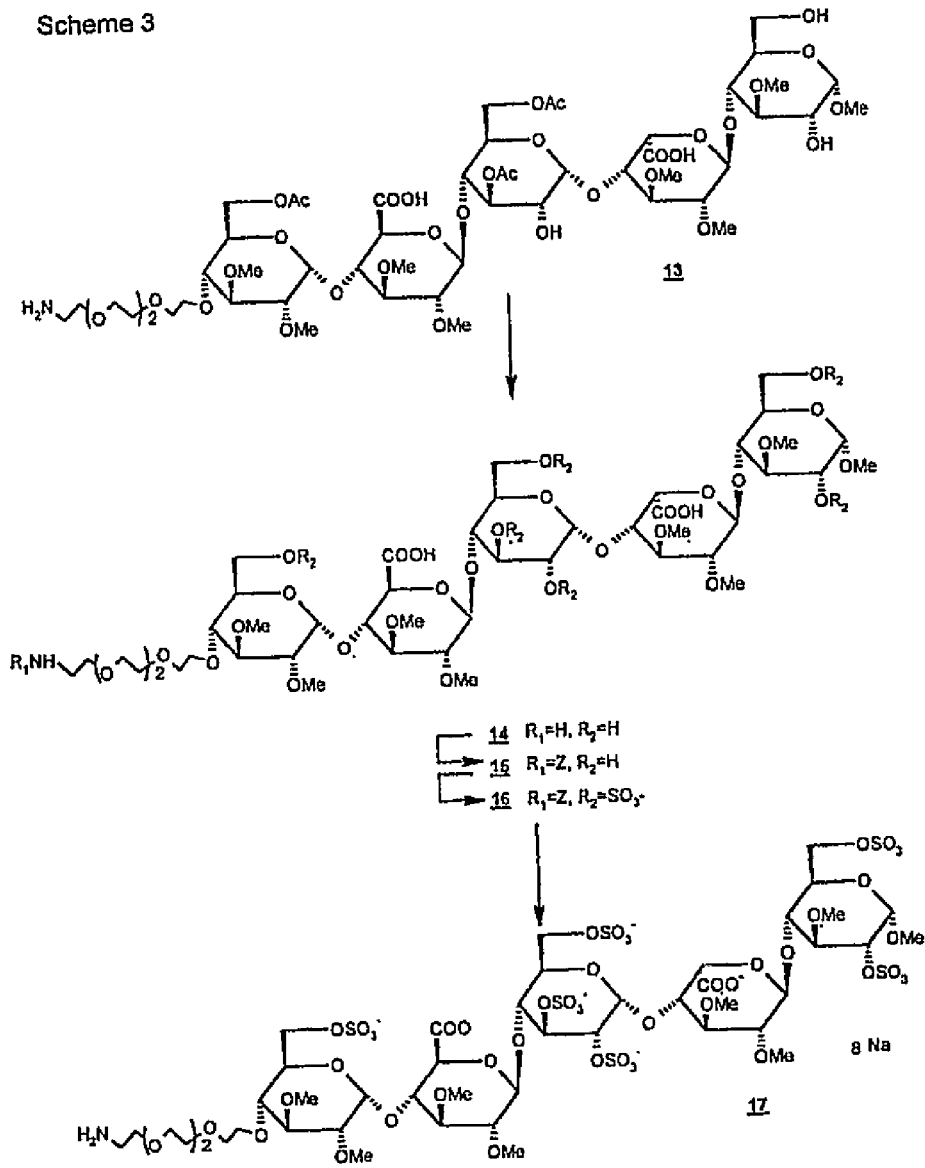

UNITED STATES PATENT AND TRADEMARK OFFICE
CERTIFICATE OF CORRECTION

PATENT NO. : 6,875,755 B2
APPLICATION NO. : 10/148868
DATED : April 5, 2005
INVENTOR(S) : Van Boeckel et al.

It is certified that error appears in the above-identified patent and that said Letters Patent is hereby corrected as shown below:

Col. 21 and 22 scheme 5 structure of compound 21, should read:

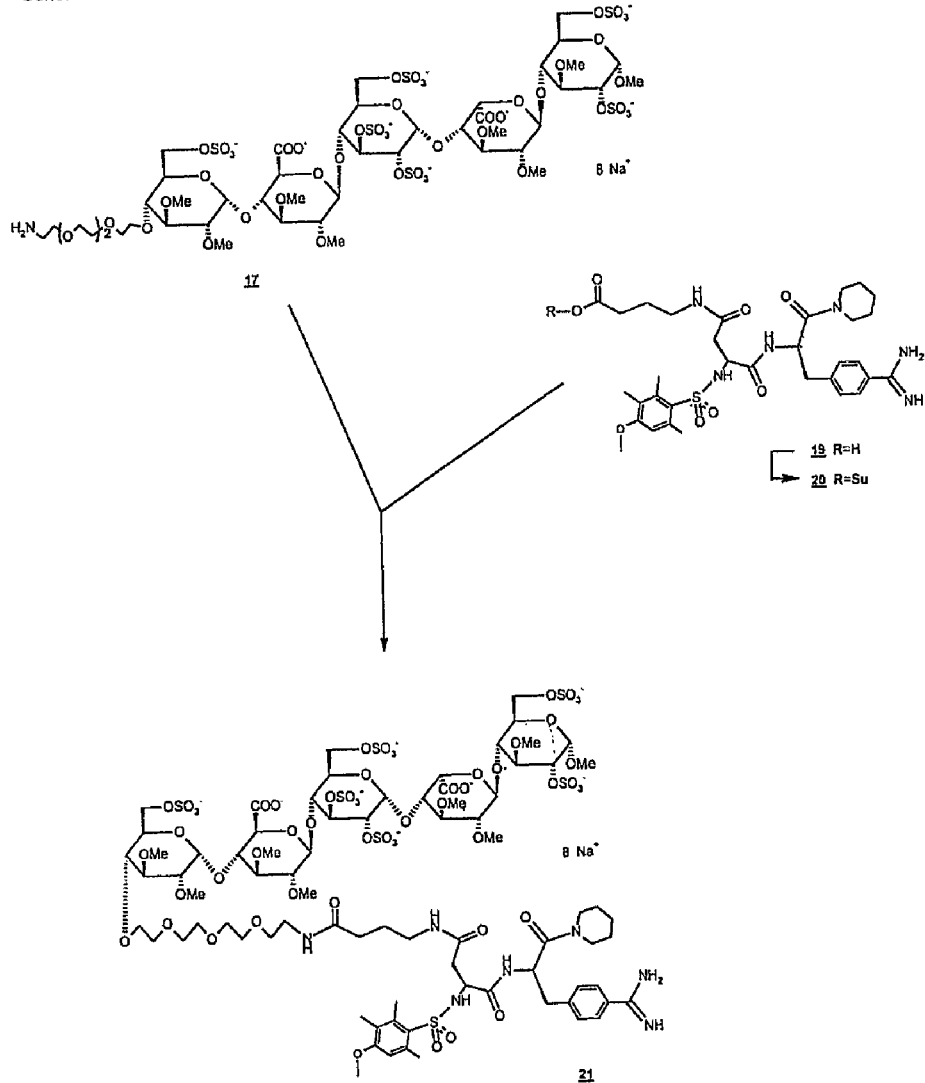

UNITED STATES PATENT AND TRADEMARK OFFICE
CERTIFICATE OF CORRECTION

PATENT NO.        : 6,875,755 B2
APPLICATION NO. : 10/148868
DATED             : April 5, 2005
INVENTOR(S)       : Van Boeckel et al.

It is certified that error appears in the above-identified patent and that said Letters Patent is hereby corrected as shown below:

Column 30, claim 1, lines 59 and 60

$(CH_2CH_2O)_p\text{-}(CH_2)_2\text{-}NH\text{-}C(O)\text{-}(CH_2)_n\text{-}NH\text{-}C(O)\text{-}(CH_2)_m\text{-},$ Column 33, claim 5, lines 44 and 45

$(CH_2CH_2O)_p\text{-}(CH_2)_2\text{-}NH\text{-}C(O)\text{-}(CH_2)_n\text{-}NH\text{-}C(O)\text{-}(CH_2)_m\text{-},$ Signed and Sealed this Sixth Day of November, 2007

JON W. DUDAS
*Director of the United States Patent and Trademark Office*